United States Patent
Kauvar

(10) Patent No.: US 6,936,427 B2
(45) Date of Patent: Aug. 30, 2005

(54) REAL TIME DETECTION OF INTERMOLECULAR INTERACTION

(75) Inventor: Lawrence M. Kauvar, Mountain View, CA (US)

(73) Assignee: Trellis Bioscience, Inc., Mountain View, CA (US)

( * ) Notice: Subject to any disclaimer, the term of this patent is extended or adjusted under 35 U.S.C. 154(b) by 482 days.

(21) Appl. No.: 10/071,844

(22) Filed: Feb. 8, 2002

(65) Prior Publication Data

US 2003/0153008 A1 Aug. 14, 2003

(51) Int. Cl.[7] ............................................. G01N 33/53
(52) U.S. Cl. ..................... 435/7.1; 435/7.92; 436/501; 436/518; 530/387.1
(58) Field of Search .......................... 435/6, 7.1, 7.92, 435/91.1, 91.2, 972; 436/501, 518, 524, 528, 173; 530/387.1, 387.3

(56) References Cited

U.S. PATENT DOCUMENTS

| | | | | |
|---|---|---|---|---|
| 6,673,901 B2 | * | 1/2004 | Koide | 530/380 |
| 2001/0055764 A1 | * | 12/2001 | Empedocles et al. | 435/6 |
| 2002/0076406 A1 | * | 6/2002 | Leung | 424/135.1 |
| 2004/0086503 A1 | * | 5/2004 | Cohen et al. | 424/143.1 |

OTHER PUBLICATIONS

Arndt et al., helix-stabilized Fv (hsFv) antibody Fragments: Substituting the Constant domains of a Fab Fragment for a heterodimeric coiled-coil Domain, J. Mol. Biol. (2001) 312, 221-228.*

Kranz et al., restricted reassociation of heavy and light chains from hapten-specific monoclonal antibodies, Proc. Natl. Acad. sci. USA, vol. 78, No. 9, pp. 5807-5811, 1981.*

Griffin et al., Specific Covalent Ibeling of Recombinant Protein Molecules Inside Live cells, Science, vol. 281, Jul. 10, 1998, pp. 269-271.*

* cited by examiner

Primary Examiner—Long V. Le
Assistant Examiner—Gary W. Counts
(74) Attorney, Agent, or Firm—Morrison & Foerster LLP

(57) ABSTRACT

Intermolecular binding can be detected by formation of a "paratope" which results in an immediate generation of a signal. The substances to be tested for interaction are bound to demitopes, wherein said demitopes are components of a paratope which binds a reporter which provides said signal when bound. Known interactions measured in this way can also be employed to screen for compounds which interfere with the interactions. In addition to testing for individual interactions, the interaction of a compound with a library or library×library interactions can also be determined and the effect of potentially interfering substances evaluated.

10 Claims, 1 Drawing Sheet

REAL TIME DETECTION OF INTERMOLECULAR INTERACTION

FIELD OF THE INVENTION

The invention is directed to methods that can conveniently be used, even in real time, to determine interactions between molecules in vitro, and in vivo, i.e., intracellularly. More specifically, the invention concerns assays which rely on the direct detection of an assembled paratope—i.e., a binary surface which binds a detectable reporter.

BACKGROUND ART

Attempts to detect intermolecular interactions have a long history. Perhaps the best known interaction assay is the yeast 2-hybrid assay which is particularly useful in detecting interactions between proteins. See, for example, Evangelista, C., et al., *Trends in Cell Biol.* (1996) 6:196–199. This assay, however, requires the presence of a relatively elaborate reporter system and is restricted to interactions which take place in the nucleus, since the detectable reporter is generated by activating transcription.

Alternatively, assays have been developed which rely on the assessment of the activity of a reconstituted enzyme. For example, the cloned enzyme-donor immunoassay (CEDIA®) is described in U.S. Pat. No. 5,643,734. In this assay, an analyte is coupled to a portion of an enzyme designated an "enzyme donor," and allowed to interact with an "enzyme acceptor" which comprises the remaining portions of the enzyme that are required for activity. In the absence of an interfering analyte binding protein, such as an antibody, this interaction occurs spontaneously and the enzyme reconstitutes itself and exhibits activity. However, when analyte binding protein is present, this reconstitution is prevented. The amount of analyte in solution can then be measured by virtue of the ability of the analyte to compete for the analyte binding protein thus permitting reconstitution of the enzyme. It is seen that this approach relies on the ability of the two portions of the enzyme spontaneously to interact; thus, the mediation of carrier substances is unnecessary and the assay is appropriate both for measuring analyte concentration, and interactions between molecules, i.e., the analyte and analyte binding protein. However, only a limited number of constructs can be made wherein an enzyme donor portion and an enzyme acceptor portion spontaneously recombine. The exemplified enzyme for CEDIA® is β-galactosidase.

Where the components of the enzyme do not spontaneously recombine, the interaction can be adapted to detect interactions between components that are coupled to each portion of the enzyme. Such an approach has been applied using dihydrofolate reductase (DHFR) as an exemplary reporting system by Remy, I., et al., *Proc. Natl. Acad. Sci. USA* (1999) 96:5394–5399; U.S. Pat. No. 6,270,964. In this system, it is necessary to supply some impetus for the reconstitution of DHFR; coupling of each portion of DHFR to a leucine zipper sequence has been found effective as a model system. This model system can be adapted to detect the interaction of any two substances where the interaction draws their coupled DHFR portions closer together. The interaction is detected, then, by assessing the activity of the enzyme. This system thus avoids the more complex reporter functions characteristic of the yeast 2-hybrid method.

An early embodiment of this type of approach is described by Johnsson, N., et al., *Proc. Natl. Acad. Sci. USA* (1994) 91:10340–10344. The molecule to be reconstituted in this case is ubiquitin which results in proteins fused thereto in being cleaved by ubiquitin-specific proteases. Because the proteolysis occurs in the proteasome, this method permits monitoring protein/protein interactions as functions of time at the natural sites of their interaction in cells.

None of the foregoing methods provide a direct immediate measurement of the interaction of two individual substances, i.e., one that does not employ a reaction cascade for detection. Neither do the results of prior art methods vary linearly with affinity. The present invention provides such results.

DISCLOSURE OF THE INVENTION

The present invention employs a pair of "demitopes" (complementary halves of a paratope, or analogs thereof), which, when assembled, provide a specific binding site for a direct reporting system. The significant aspect of the present invention is that the proximity of the two demitopes creates an immediate readout of this proximity for example, by acquisition of fluorescence, fluorescence quenching, or alteration of an NMR signal, or by binding of an enzyme or toxin to the paratope. When each of the demitopes is coupled to a substance whose interaction is to be tested, the interaction of the coupled substances results in an immediate signal.

Thus, the invention provides an immediate and direct detection of the interaction between substances to be tested, which is directly proportional to the strength of the interaction. The interaction can be detected based on a single interaction between two candidate molecules, or can be applied to compound×library or library×library interaction screening. The basis for the invention is creation of a paratope wherein the creation of the paratope results in an immediate signal of its creation by creating a new microenvironment for the binding of the reporter.

Thus, in one aspect, the invention is directed to a method to detect an interaction between a first substance and a second substance which method comprises providing said first substance coupled to a first demitope and said second substance coupled to a second demitope and combining a sample containing said first substance with a sample containing said second substance. The formation of a paratope from the two demitopes results if the first substance interacts or binds with the second substance. The formation of the paratope results in binding a reporter that generates an immediate signal. Thus detection of signal indicates the interaction between said first and second substance and failure to signal detect indicates the lack of interaction between said substances.

It is an essential feature of the invention that the paratope will not form unless the first and second substance interact. That is, the dissociation constant for the interaction being studied should be smaller than the dissociation constant for the components of the paratope. It is preferable that the affinity of the assembled paratope for the reporter be even higher than that for the two substances so that any successful interaction will pick up a reporter moiety.

Since the interaction of any two substances can be detected, the general method can be employed to identify substances that will interfere with a known interaction as well as for finding evidence of interacting substances whose relationship was not previously known. Thus, in another aspect, the invention is directed to a method to identify a candidate compound which interferes with a known interaction between two other compounds, such as a ligand and receptor or antibody and antigen which comprises conducting the above described method in the presence and absence of the compound and comparing the signals obtained whereby a reduction in the signal which indicates the interaction in the presence as opposed to the absence of the compound indicates that the compound interferes with the interaction.

In another aspect, the invention is directed to constructs whereby substances to be tested are coupled to demitopes. Significant embodiments of this aspect include coupling of said first substance to the variable region of a heavy chain of an immunoglobulin and coupling the second substance to the variable region of the light chain of said immunoglobulin.

Because the signal is generated immediately upon interaction of the substances to be tested, the method of the invention lends itself to simultaneous observation of a number of interactions as well as to observations of interactions which occur intracellularly and which can be observed using microscopy, or by NMR from outside a living animal.

The invention also includes kits which contain the components and instructions for carrying out the method of the invention.

MODES OF CARRYING OUT THE INVENTION

Prior art methods of determining interactions between substances rely on complex reporting systems which are not immediate or proportional to affinity and thus preclude real time tracking of the interaction either in vitro or in vivo. The present invention provides methods whereby real time detection is possible by virtue of the immediate reporting of paratope formation.

By "immediate" reporting is meant two things. First, there is no cascade of reactions needed to obtain a detectable signal. The signal flows directly from the binding of the reporter to the paratope. Second, the response is linear—i.e., the stronger the binding of the two substances to be tested, the greater the readout resulting from the reporter. Thus, for example, if the reporter binding is detected by fluorescence quenching, the magnitude of the quenching will be directly proportional to the strength of the interaction of the two substances to be tested.

Figure 1A:
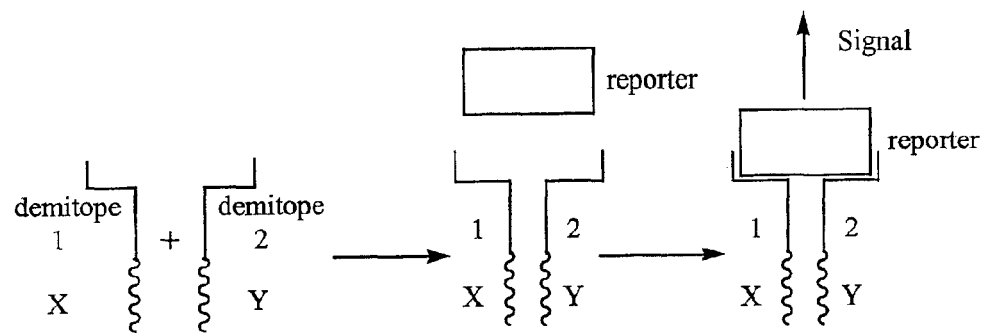
FIGS. 1A and 1B show, diagrammatically, alternative embodiments of the invention.
Figure 1B:
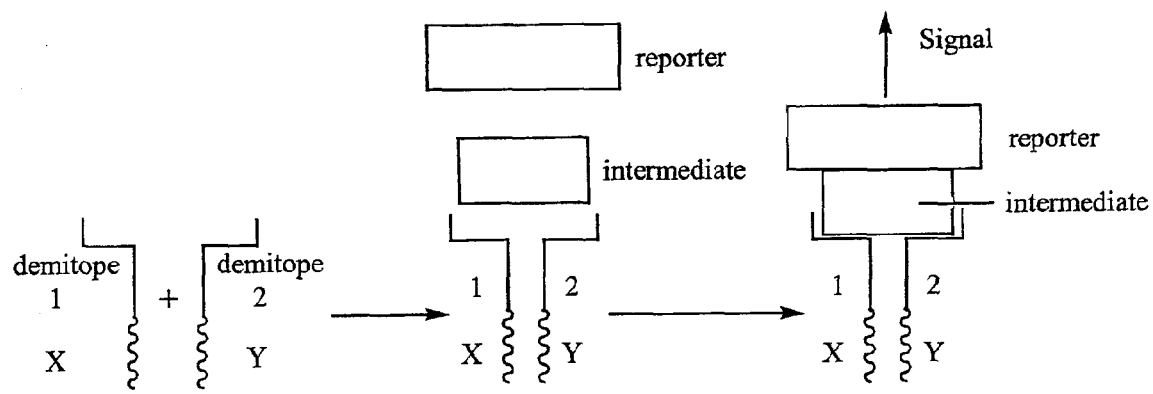

As used herein, the word "paratope" refers to a molecular configuration which will create a microenvironment for binding to a reporting system that provides an immediate signal when the paratope is formed. As diagrammed in FIG. 1A, the paratope useful in the invention is obtained by the assembly of two demitopes, neither of which is able to bind a signaling moiety individually, but which when assembled form a "paratope" which is able to do so. Thus, demitopes 1 and 2 are brought into proximity when substances X and Y interact; these demitopes then form a complete paratope which is able to bind a reporter, signal generating moiety. In a modification of this embodiment, shown in FIG. 1B, the reporter is attached to the formed paratope through a secondary interaction; for example, the formed paratope may bind biotin, which then can couple to a biotinylated enzyme that can be assayed directly.

To determine whether a candidate substance is able to interfere with the interaction between X and Y, the demitope containing X and the demitope containing Y are allowed to interact in the presence of the candidate compound as well as in its absence. The signal generated by the reporter would be reduced in the presence of the candidate compound if interference in the interaction between X and Y occurs.

As is evident from the foregoing explanation, the demitopes useful in the invention methods must be "complementary." That is, they must, when assembled, form a paratope. When assembled, the paratope is able to bind a reporter substance which emits a signal upon binding or the paratope binds an intermediate compound which in turn binds the signal generating reporter.

Thus, as specifically used in the present application, the word "paratope" refers to the resultant of the assembly of two demitopes which, when assembled, provide an immediate signal of their assembly. The paratope achieves this by directly binding a signaling moiety whose signaling characteristics are immediately apparent upon binding, and where the signal characteristic is proportional to binding affinity.

One example of a paratope comprises the combination of variable regions of light chain and heavy chain of an immunoglobulin which when assembled, are able to bind a reporter, such as a fluorescent indicator.

While the use of two variable regions to create a paratope is perhaps the most convenient and easiest to implement, even in the absence of prior knowledge of the nature of the interaction between with paratope and signaling moiety, other embodiments of the demitopes can readily be envisioned. Any binding agent which can be created to a specific ligand wherein the ligand is itself, or is coupled to, a signaling moiety might be used. For example, two portions of a receptor, when assembled, would have the ability to bind the ligand for receptor. Ligands which are specific for receptors are altered in at least some of their properties when bound as opposed to their properties when free in solution. In particular, this is almost always the case with respect to NMR spectra. The ligand itself may also be fluorescent wherein its fluorescence may be quenched or stimulated by binding to the ligand, or its absorption spectrum properties may be altered. A fluorescent molecule which is not itself the ligand may also be used by coupling the ligand to a fluorescent moiety which is then brought into proximity for the receptor will serve as an adequate signaling reporter. All of these are immediate alterations and could be used as an index for molecular interactions.

If a fluorescent indicator is used, it may exhibit enhanced fluorescence by virtue of this binding, or exhibit diminished fluorescence by virtue of this binding. Alternatively, the demitopes, when assembled, may bind moieties which change other characteristics when they are bound, such as changes in NMR spectrum.

Examples of such paratopes and interactions are described in the literature. For example, Kranz, D. M., et al., *Proc. Natl. Acad. Sci. USA* (1981) 75:5807–5811 took advantage of the ability of assembled variable regions to quench the fluorescence of bound fluorescein in order to monitor immunoglobulin recombination and active site formation. When antibodies containing κ light chains with IgG1 or IgG2 heavy chains were allowed to immunoreact with fluorescein, the fluorescence of fluorescein was quenched more than 90%. Thus, fluorescence quenching was a practical way to monitor reconstitution and active site formation on mixing resolved heavy and light chains. In this case, the heavy and light chains are the demitopes and the resulting associated combination is the defined paratope which, upon binding fluorescein, provides the immediate signal of fluorescence quenching. The system of Kranz is adapted to the method of the invention by coupling the light chain to a first substance whose interaction with a second substance is to be tested and coupling the heavy chain variable region to the second substance. Interaction between the first and second substance will then reassemble the active site and result in a paratope which quenches the fluorescence of fluorescein.

Rothstein, T. L., et al., *Mol. Immunol.* (1983) 20:161–168 used a similar phenomenon, that of fluorescence quenching of p-azophenylarsonate by various anti-idiotypic antibodies, as a measure of affinity of the antibody for the dye. The higher the fluorescence quenching by virtue of the binding of the dye to antibody, the higher the affinity. Thus, a paratope of predetermined affinity directed against p-azophenylarsonate may be used to send an immediate signal upon paratope formation due to binding of the dye. With appropriate calibration, the magnitude of quenching may be used as an index of the affinity created in the paratope and this affinity is proportional to the strength of the interaction of the substances whose interaction accounts for the paratope formation. The system of Rothstein is adapted to the method of the invention by coupling each of the heavy and light chains of the variable regions of a defined antibody against p-azophenylarsonate and detecting fluorescence quenching as a measure of the strength of the interaction of the two coupled substances.

The phenomenon of fluorescence quenching by binding to a paratope is not limited to organic fluorescent molecules. Metal-based complexes may also exhibit quenching upon sequestration in organic environments, such as by binding to antibodies or assembled receptors. For example, fluorescence quenching of rubidium complexes occurs upon binding to antibodies raised against such complexes as described by Shreder, K., et al., *J. Am. Chem. Soc.* (1996) 118:3192–3201.

The immediate signal generated may not necessarily involve quenching of fluorescence, but may, depending on the fluorophore and the paratope, be fluorescence enhancement. For example, as shown by Parker, C. W., et al., *Biochemistry* (1967) 6:3417–3427, antibodies raised against ε dansyl lysine effect a 150-fold enhancement of the fluorescence of ε dansyl lysine when the fluorescent compound is bound to the antibody.

Other examples of instances where fluorescence is altered by binding to an organic molecule, such as the paratope of an antibody, or any other assembled paratope include the binding of "Quantum Dots" which are clusters of metal atoms. Their fluorescence properties are greatly enhanced and tuned to a narrow emission frequency by appropriate molecular environments as described in U.S. Pat. No. 6,207,392 and by Bruchez, Jr., M., et al., *Science* (1998) 281:2013–2016.

Similarly, the NMR properties of compounds are often influenced by their environment, specifically their ability to interact with water molecules. For example, an assay has been described which is based on enzymatic cleavage of a gadolinium containing compound to expose the metal to water, thereby drastically changing the NMR spectrum (*Angew. Chem. Int. Ed. Engl.* 36:726 (1997)).

In summary, one method of signaling the formation of a paratope comprises the resulting enhancement or quenching of fluorescence of a single molecule when it is paratope-bound.

Thus, in one embodiment, the method of the invention employs substances to be tested each coupled to a demitope wherein the demitopes are assembled when the substances interact to obtain a paratope, which paratope is then able to bind a fluorescent molecule. By virtue of the binding, the fluorescence of the bound molecule is modulated as compared to the fluorescence of the reporter in solution. One convenient form of a paratope in this embodiment is a variable region of an immunoglobulin; the demitopes are thus the heavy and light chain variable regions. However, this embodiment is not limited to the illustration of forming a variable region; a paratope might be formed, for example, by a receptor where the demitopes are portions of the receptor and either the ligand for the receptor is itself fluorescent or is bound to a fluorescent molecule. Similarly, in the case of the use of variable regions as paratopes, the fluorescent indicator need not be bound directly but can be coupled to a hapten for the variable region.

While modulation of fluorescence by virtue of environmental changes caused by binding is a useful form of detection, other measurable phenomena can also be used. For example, it is known that the immediate environment affects the nuclear magnetic resonance spectrum of reporter molecules as described by Moats, R. A., et al., *Angew. Chem. Int. Ed. Engl.* (1997) 86:726–728. Any signal which is generated or altered by virtue of binding directly to a paratope can be used in this embodiment. NMR is of particular interest since many distinguishable signals can be generated, allowing multiple interactions to be studied concurrently. Further, the signals can be detected from a live organism.

Other types of reporters may also be used. These reporters also may be bound directly or through an intermediate adapter moiety. In one example, the reporter molecule itself is an enzyme which can be bound to the paratope either directly or through, for example, biotinylation where the enzyme binds to biotin. The activity of the enzyme can then be detected through its concentration on antibody immobilized to a solid support. Thus, in this embodiment, the assembled paratopes are coated on a solid support and the retention of the enzyme on the solid support assessed by typical enzyme-mediated reactions.

In another alternative, the assembled paratope would bind a toxin as a reporter, either directly or through an intermediate binding moiety. The toxin, having been sequestered by the paratope, loses its toxicity and thus when assembly has occurred, the concentration of toxin is reduced. The inactivation of the toxin then permits cell growth so that only cells in the presence of positive interactions will proliferate. This approach is particularly attractive for library×library screening; a library of compounds, e.g. peptides or nucleotide sequences, is coupled to demitope A and a library of substances to be cross-tested is coupled to demitope B. Demitopes A and B are complementary, and the attachment is such that interaction of the demitopes to form a paratope can occur by virtue of the interaction of the attached molecules. The constructs of [demitope A-library] and [demitope B—library] are prepared as expression vectors either as plasmids or phage and used to transfect or infect large numbers of bacteria or other suitable host cells. Each phage or plasmid may be labeled with a selectable marker so that only doubly-infected cells are selected. For example, the first library coupled to demitope A may reside on a plasmid or phage with tetracycline resistance as a selectable marker and demitope B attached to the second library resides on a phage or plasmid using ampicillin resistance as a selectable marker. The transfected or infected microorganisms are then grown under selection conditions so that only bacteria which contain a member of each library survive. If toxin is added to the culture, only those bacteria where an association has taken place between members of the library will proliferate. The toxin may also be provided intracellularly through transfection or infection with a third expression vector, with a third selectable marker. Alternatively, if the toxin effects phage replication, only those bacteria wherein interaction has occurred will produce replicating phage. Diluting the culture to independent colonies or plaques permits assay of those members of the library which interact. This permits large numbers of library members to be assessed since only successful individual colonies will be formed. As many as $10^{13}$ phage could be screened against as many as $10^4$ cDNA derived proteins, for example.

The foregoing assay could also be made at least semi-quantitative by varying the conditions of toxicity. For example, if the toxin is more lethal at higher temperatures, gradation in temperature could be used to titrate binding affinity since the more tightly the toxin is bound the less toxic it becomes. Alternatively, the toxin concentration itself could be varied.

As an alternative to plating at limiting dilution, laser microdissection may be employed to pick colonies which show successful interaction. That is, established techniques exist for creating/destroying "glue" (polymer encasing the cells) by action of laser light, as commercialized by Arturus, Inc. Cells which have productive interactions that generate a signal can be identified by inspection and "glued" or "unglued" by a pulse of laser light. The retained or liberated cells (or colonies) can then be extracted.

As set forth above, the two demitopes thus can assume a number of forms. Perhaps the most convenient form is that of the variable regions of heavy and light chains from a common variable region of a single antibody. A convenient way to obtain appropriate variable regions is to construct, recombinantly, single chain antibodies (scFv) which contain variable regions derived from heavy and light chains coupled to a linker. In this embodiment, a suitable paratope for binding and affecting the signal molecule can then be empirically obtained using standard phage display techniques as described by Marx, C., et al., *New England J. Med.* (1996) 335:730–733. A multiplicity of candidate paratopes can be provided by phage display, and those which successfully bind the signaling moiety and alter its signaling characteristics can be recovered by routine experimentation. Once the correct paratope is identified, the linker between the two variable regions can, in theory, be cleaved proteolytically to obtain the demitopes. However, much more conveniently, the nucleotide sequence encoding the scFv is cleaved. The DNA encoding each of the two variable regions is then used to construct the demitope for coupling to a test substance. The availability of nucleotide sequences encoding the heavy and light chain and variable chain regions is also helpful in that these can be mutagenized so as further to weaken their intrinsic attraction for each other. This distances the values of the dissociation constants of the demitopes from those of the substances to be assessed. This approach is particularly convenient when the substances to be tested for interaction are proteins. Fusion proteins are then readily generated between the light chain portion and the first substance and the heavy chain portion and the second substance for example.

Just as the embodiments of the demitopes are multiple, the substances whose interactions are to be evaluated cover a wide range. It is only necessary to couple a first substance to be evaluated to a first demitope and a second substance to be evaluated to a second demitope. The interaction to be observed may be between two proteins, proteins and nucleic acids, nucleic acids and nucleic acids, proteins and small molecules, nucleic acids and small molecules, carbohydrates and proteins, carbohydrates and small molecules, and any other imaginable interaction for which information is desired. It remains only to attach the candidates to the demitopes to carry out the method of the invention.

If the substances to be evaluated and the demitopes are both proteins, the most straightforward method of attachment is the formation of fusion proteins. On the other hand, if one of the substances is a small molecule and the demitopes are proteins or vice versa, chemical coupling to the paratope is indicated. One of ordinary skill will understand the appropriate method to couple the substances to be tested to the two demitopes.

As an alternative embodiment, the demitopes could be composed of DNA or RNA, wherein the assembled paratope would function as an aptamer. If the demitopes are attached to adjacent sequences complementary to a particular mRNA, then its appearance can be monitored. Alternative splicing can thus also be readily assayed. Drugs that modulate alternative splicing can thereby be conveniently discovered, of particular interest in regard to viruses that use alternative splicing to increase the information content of their small genomes.

The procedure, then, is simply to bring into proximity a first sample which contains a first demitope coupled to a first substance whose interaction is to be tested with a second sample containing a second substance coupled to a second demitope (which is complementary to the first) coupled to a second substance whose interaction is to be tested wherein the formation of the paratope formed by binding of the first substance to the second substance will result in binding a reporter which gives an immediate signal. Mixing of these samples may be conducted in vitro, but may also occur within cells or within whole organisms. It is known to be possible to detect signals from within whole organisms of the type discussed above. For example, Contag, P. R., et al., *Nature Medicine* (1998) 4:245–247 describe the detection of light from luciferase generated from within an organism; a multiplicity of reports of detecting NMR signals is also available.

Once an interaction between moieties X and Y is detectable by virtue of the attached demitopes binding a reporter, compounds can be screened that disrupt the interaction of X and Y. In this application, X and Y are typically substances which are known to interaction and therefor which would, in the absence of an interfering compound, cause the reporter to generate a signal. For example, an antibody/antigen interaction or a ligand/receptor interaction might be used. Thus, compounds that interfere with the ability of a pharmaceutical or native ligand to agonize or antagonize a receptor are identified by the methods of the invention. In this regard, it is convenient to provide related X' and Y' assays, where X' and Y' are compounds similar to, but not identical to X and Y, as specificity counterscreens. The multiplicity of potential reporters, each recognized by a different assembled paratope, is thus a desirable aspect of the invention. Thus, it would be possible in a single reaction mixture to test a multiplicity of X—Y and X'—Y' interactions either for the purpose of screening potentially interfering compounds or for detecting multiple interactions between X and Y (and X' and Y') since the demitopes can be coupled to a variety of signaling moieties which are distinguishable when observed simultaneously. This is further described in the succeeding paragraphs.

While it is easiest to describe conduct of this assay as between only a first and second candidate substance, it should be apparent that it is also possible to use the principles described herein to design assays wherein entire libraries of substances are assessed either against a single substance or against a library of second substances. It may be convenient to label the various classes of substances in the library differentially—i.e., to attach each member of a subclass of the library to a different demitope which, when coupled, will form a paratope whose signal is distinct.

For example, single chain antibodies are prepared which immunoreact with fluorescein, dansyl lysine, various Quantum Dots, or a multiplicity of other fluorescent compounds. Each pair of variable regions can be attached to various members of libraries of proteins, small molecules, or other substances to be tested. In one approach, all heavy chain regions might be attached to a single substance which is to be interrogated for binding to a library of substances each attached to a different light chain variable region. Alternatively, both heavy and light chains can be attached to a multiplicity of regions and the interactions discriminated by the wavelength of the fluorescence. By determining in advance which substances are attached to which variable regions, simple identification of the wavelength of fluorescence will identify the nature of the interaction.

In more detail, antibodies could be prepared against fluorescent molecules 1–5, each of which has a different fluorescent wavelength. A "library" of five candidate substances is coupled to the light chains of these antibodies—i.e., substance 1 to light chain of antibody, which binds dye No. 1; substance 2 to light chain of antibody which binds dye No. 2 and so forth. The heavy chains of these antibodies can be coupled to, for instance, substance A. If, upon mixing the coupled light and heavy chains along with the fluorescent dyes, modulation of dyes Nos. 3 and 4 is observed, it can be determined that substance A binds to substances 3 and 4, but not to substances 1, 2 and 5.

Observation of multiple interactions is particularly advantageous when the reporter signal is measured using microscopy. Thus, employing wide field microscopic techniques, such as those described in U.S. application Ser. No. 09/394, 842, incorporated herein by reference, a multiplicity of interactions can be simultaneously observed in real time. NMR offers similar advantages.

The ability to image intracellular fluorescence has been demonstrated on a number of occasions. For example, Farinas, J., et al., *J. Biol. Chem.* (1999) 274:7602–7606 describe trapping hapten-fluorophore conjugates, In this work, a cDNA encoding a single chain antibody which was fused with sequences targeting the variable regions to the Golgi apparatus was used to generate a "receptor" for the hapten-fluorescent probe. By utilizing this fluorescent probe, changes in pH (which alter the fluorescence of the probe) were monitored at this cellular location using microscopic techniques.

Of course, alternative fluorescent probes have been observed intracellularly and are useful in tracking intracellular events. Green fluorescent protein, for example, has been commonly used in this context. Green fluorescent protein is useful in the present invention as a label as well. It should be noted that "green fluorescent protein" can come in a variety of colors which are a function of variations in the amino acid sequence. The term "green fluorescent protein" is simply historical as the original proteins, isolated from fluorescent organisms fluoresced in the green portion of the spectrum. In addition, Griffin, B. A., et al., *Science* (1998) 281:269–272, describe a technique for labeling individual cellular proteins with fluorescent probes and tracing their intracellular location.

As described above, the present application offers, in addition to intracellular tracking of single interactions between cellular proteins, the opportunity to observe simultaneously multiple intracellular protein interactions. Multiple interactions can also be observed in vitro using similar techniques.

The invention also includes kits designed for the practice of the method of the invention. Typically, these kits will contain, in separate containers, the complementary demitopes to which the substances to be tested are to be bound. It may be convenient to include reagents for coupling substances to the demitopes as well. The kit may also include a reporter system for signal generation when the demitopes combine to form a paratope. The reporter may also, of course, be supplied separately. As described above, the reporter may be a single substance directly interacting with the paratope whose own properties are altered upon binding, or the reporting system may involve an intermediate which binds the paratope but where the intermediate in turn binds the signaling moiety. Preferably, the intermediate and signaling moiety are previously coupled when supplied to the reaction mixture. As described above, the reporter may be a fluorescent molecule which binds the paratope, a fluorescently labeled moiety which binds the paratope, an enzyme or toxin which directly binds the paratope or an enzyme or toxin coupled to an intermediate which binds the paratope. The demitopes themselves are conveniently heavy and light chains of antibody variable regions, or are portions of a receptor which binds a ligand. Kits may also be prepared where the substances in a library are pre-assembled with one of the demitopes; such libraries are convenient sources of candidate molecules for binding to a substance for which a binding partner is sought. The construction of a kit for conduct of the method will depend on the particular format chosen.

What is claimed is:

1. A method to determine whether a first substance interacts with a second substance or to determine the affinity of the first substance for a second substance which method comprises contacting said first substance coupled to a first demitope with said second substance coupled to a second demitope complementary to the first demitope, wherein said substances are heterologous to the demitopes, and their interaction and affinities are not known, in the presence of a reporter, wherein said first and second demitopes, when assembled, form a paratope which binds said reporter, and wherein said reporter generates an immediate detectable signal when bound to the paratope, and determining the presence, absence or magnitude of the signal produced;

wherein the presence of the signal indicates said first and second substances interact and the absence of signal indicates the first and second substance do not interact, or the magnitude of the signal is a measure of the affinity of interaction of said first substance and said second substance.

2. The method of claim 1, wherein said first and second demitopes are variable regions of the heavy and light chain of an immunoglobulin.

3. The method of claim 1, wherein said first and second demitopes are portions of a receptor.

4. The method of claim 1, wherein said immediate detectable signal is fluorescence quenching or fluorescence enhancement.

5. The method of claim 1, wherein said immediate detectable signal is an alteration of nuclear magnetic resonance (NMR) spectrum of the reporter.

6. The method of claim 1, wherein said immediate detectable signal is the effect of a toxin.

7. The method of claim 1, which is conducted intracellularly.

8. The method of claim 1, wherein the immediate detectable signal is observed by wide-field microscopy.

9. The method of claim 1, wherein the presence or absence of signal is determined.

10. The method of claim 1, wherein the magnitude of the signal is determined.

* * * * *